United States Patent

Epstein et al.

Patent Number: 5,514,183
Date of Patent: May 7, 1996

[54] REDUCED FRICTION PROSTHETIC KNEE JOINT UTILIZING REPLACEABLE ROLLER BEARINGS

[76] Inventors: Norman Epstein, Rte. No. 301, Carmel, N.Y. 10512; Steven B. Zelicof, 12 Seneca Rd., Scarsdale, N.Y. 10583

[21] Appl. No.: 359,515

[22] Filed: Dec. 20, 1994

[51] Int. Cl.⁶ ........................................... A61F 2/38
[52] U.S. Cl. ................................. 623/20; 623/18
[58] Field of Search ................. 623/20, 19, 18, 623/22, 16

[56] References Cited

U.S. PATENT DOCUMENTS

| | | | |
|---|---|---|---|
| 4,262,368 | 4/1981 | Lacey | 3/1.911 |
| 4,358,859 | 11/1982 | Schurman et al. | 3/1.911 |
| 4,673,408 | 6/1987 | Grobbelaar | 623/20 |
| 4,865,606 | 9/1989 | Rehder | 623/20 |
| 4,919,660 | 4/1990 | Peilloud | 623/20 |
| 5,011,496 | 4/1991 | Forte et al. | 623/20 |
| 5,037,439 | 8/1991 | Albrektsson et al. | 623/20 |
| 5,116,375 | 5/1992 | Hofmann | 623/20 |
| 5,147,406 | 9/1992 | Houston et al. | 623/20 |
| 5,176,684 | 1/1993 | Ferrante et al. | 606/86 |
| 5,197,987 | 5/1993 | Koch et al. | 623/20 |
| 5,314,480 | 5/1994 | Elloy et al. | 623/20 |

*Primary Examiner*—David Isabella
*Attorney, Agent, or Firm*—Parmelee, Bollinger & Bramblett

[57] ABSTRACT

A roller bearing knee replacement joint is provided in which a femoral component attached to the surgically prepared distal femur is positioned for articulation on a tibial component, which simulates the articulating surface of the natural tibia. The articulating surface has replaceable roller bearing units which provide the contact with the femoral component. A bearing mounting member has spaced bearing unit receptacles which are adapted to receive the bearing units laterally and permit the lateral removable therefrom. The roller bearing units reduce friction between the components and may be replaced with less extensive surgical procedures than in other replacement procedures. A patella component has a patella button which rides in a central concave groove in the femoral component and is mounted on radial roller bearings to provide rotational movement for the patella button to emulate the motion of a natural patella.

8 Claims, 5 Drawing Sheets

REDUCED FRICTION PROSTHETIC KNEE JOINT UTILIZING REPLACEABLE ROLLER BEARINGS

BACKGROUND OF THE INVENTION

This invention relates to prosthetic knee joints, and more particularly to a roller bearing knee replacement which can be used with presently employed knee prosthesis equipment and procedures, while providing less friction by utilizing replaceable roller bearings.

The artificial knee joint generally includes a femoral component, a tibial component and a patella component. The distal femur of the recipient is surgically prepared to receive and have secured thereto the femoral component which is used to simulate the articulating surface of the natural femur. The tibial component is secured to a surgically prepared proximal tibia and is used to simulate the articulating surface of the natural tibia. The tibial component carries a liner or insert bearing surface mounted on a metal backed surface. The insert bearing surface is made of ultra-high molecular weight polyethylene (UHMWP) or other suitable material which is in frictional engagement with the femoral component bearing the full weight of the user. Accordingly, this liner or bearing surface is subject to wear, which eventually could cause a major breakdown of the joint, thereby requiring extensive surgery.

SUMMARY

Accordingly, it is an object of this invention to provide a new and improved knee replacement joint which is subject to less friction for increasing the longevity of the knee prosthesis.

Another object of this invention is to provide a new and improved prosthetic knee joint having separate replaceable roller bearing units which do not require major reconstructive surgery for repairing the prosthetic knee joint.

In carrying out this invention in one illustrative embodiment thereof, a reduced friction knee joint prosthesis includes a femoral component having a pair of spaced lateral condyle carriers connected by an intercondylar connector which carriers are adapted to house resected femoral condyles and a tibial component having a bearing mounting member therein. Bearing means having a bearing race means containing a plurality of roller bearings are mounted in said bearing mounting member, and the femoral component is positioned on the roller bearings for pivotal movement on the roller bearings mounted in said tibial component.

BRIEF DESCRIPTION OF THE DRAWINGS

This invention together with further objects, aspects, features and advantages thereof, will be more clearly understood from the following description taken in connection with the accompanying drawings.

DESCRIPTION OF THE PREFERRED EMBODIMENTS

Figure 1:
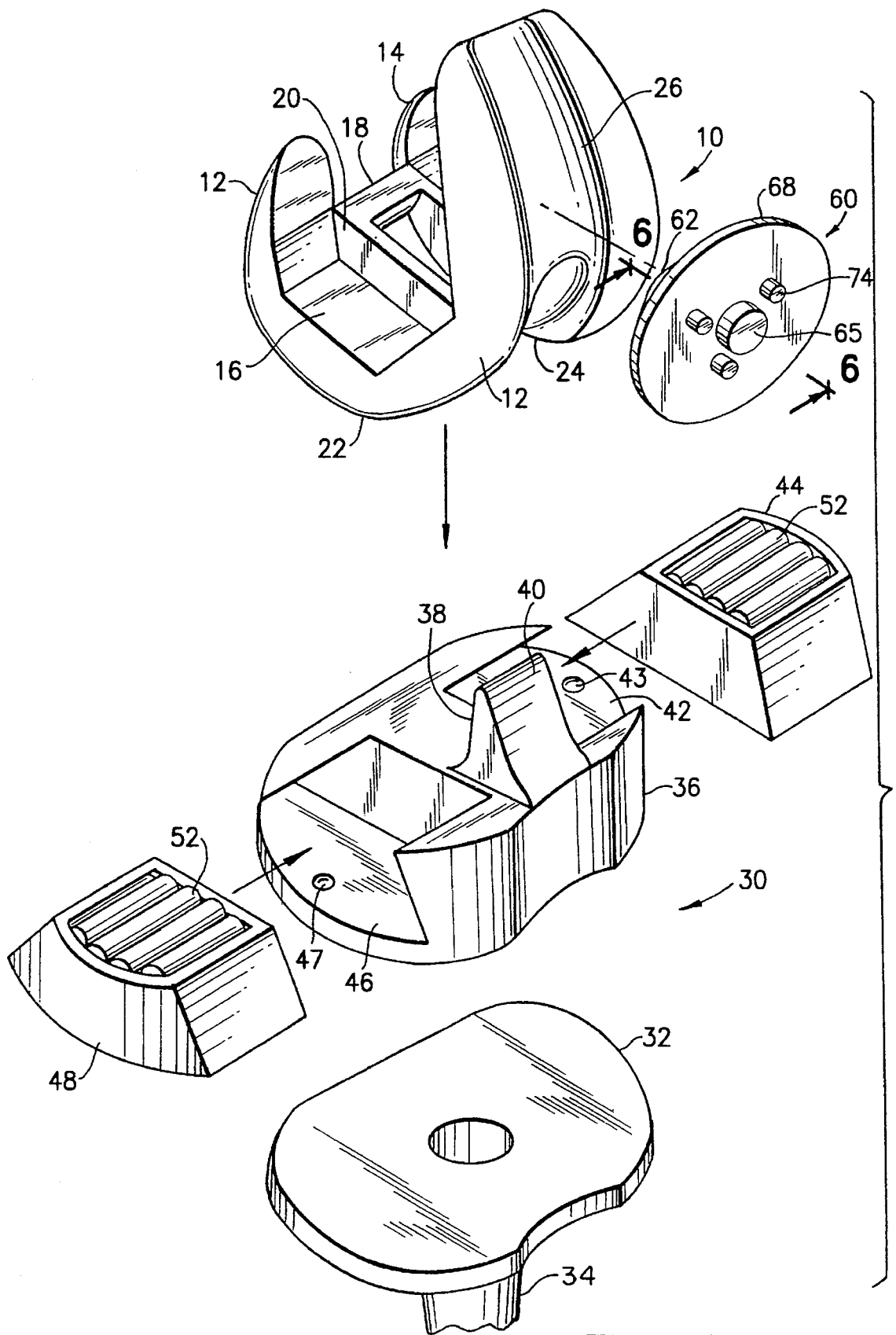
FIG. 1 is an exploded perspective view of the prosthetic knee joint of the present invention.

Referring now to FIG. 1, the prosthetic knee joint of the present invention comprises a femoral component, referred to generally with the reference numeral 10 and a tibial component, referred to generally with the reference numeral 30 and a patella component, referred to generally with the reference numeral 60. The femoral component 10 has a pair of laterally spaced condyle carriers 16 linked by an intercondyle connector 18 having an opening 20 therein. The femoral component 10 has condylar contact surfaces 22 and 24 on the bottom of the condyle carriers 12 and 14, respectively terminated in an anterior curved upwardly extending patella plate section 26, which is adapted to receive the patella in a recess therein, which will be described hereinafter.

The tibial component 30 has a tray 32 carrying a mounting post 34 which is adapted to be implanted in the tibia. A bearing mounting member 36 is mounted on the tray 36. The bearing mounting member 36 has a stabilizing post 36 with a curved posterior cam surface 40 thereon. A pair of laterally spaced bearing receptacles 42 and 46 have detents 43 and 47, respectively. The bearing receptacles 42 and 46 have open sides for the lateral insertion therein of bearing units 44 and 48, respectively. The bearing units 44 and 48 each have a bearing race 50 (see FIG. 3) for housing for captive race movement therein of a plurality of roller bearings 52. The bearing units have a modified trapezoid shape, the outer wall being curved to conform with the ovular tray 32 (see FIG. 5). The bearing units can be removably inserted in the bearing receptacles through the open side walls of the receptacles and are releasably retained therein by the detents 43 and 47.

Figure 2:
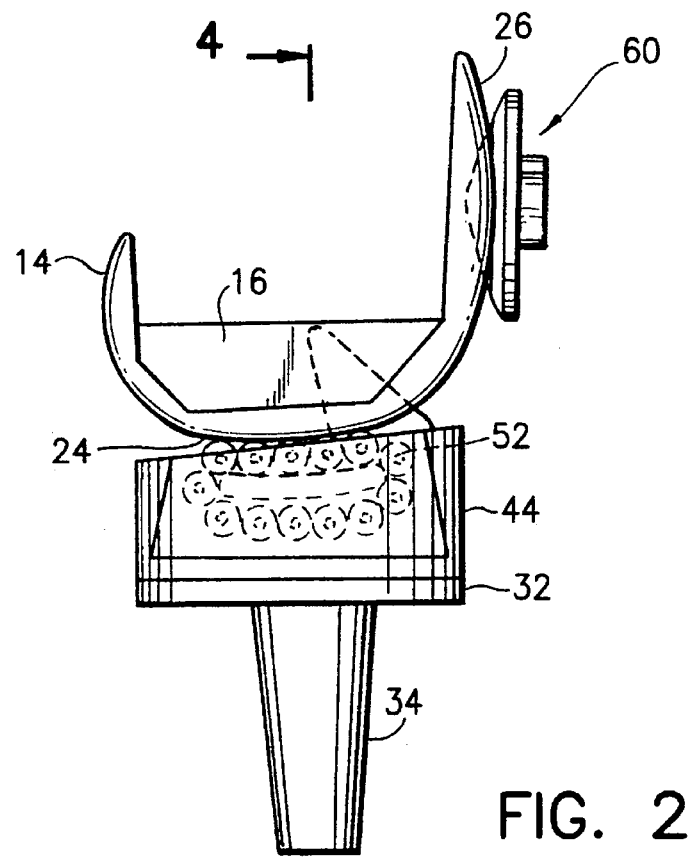
FIG. 2 is a side elevational view of the prosthesis knee joint shown in FIG. 1 showing roller bearings in phantom.
Figure 3:
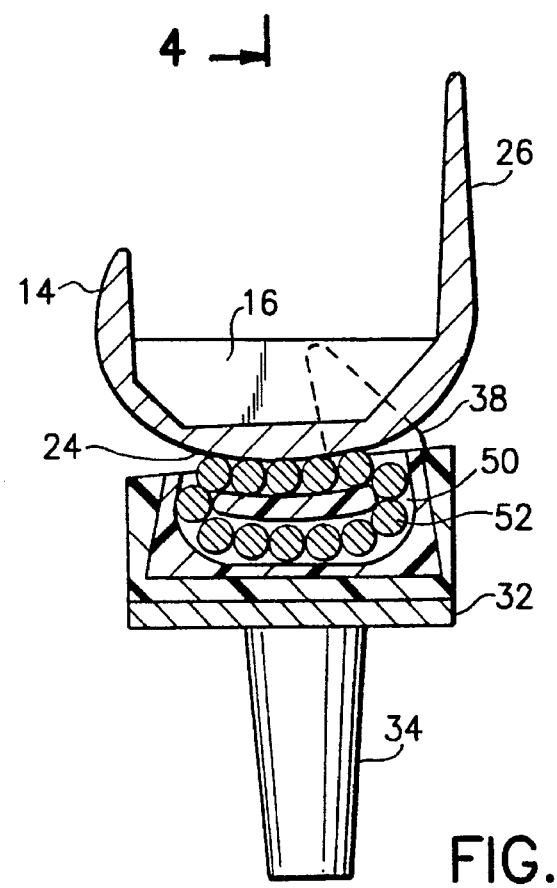
FIG. 3 is a cross-sectional view taken along line 3—3 of FIG. 4.

As will be seen in FIGS. 2 and 3, the bearing surface 24 of the condyle carrier 24 rests on the roller bearings 52 which are slightly downwardly inclined in the bearing unit 44 forming a slightly concave configuration for receiving the convex bearing surface 24. The stabilizing post 38 rides in the connector opening 20 in the femoral component 10.

Figure 4:
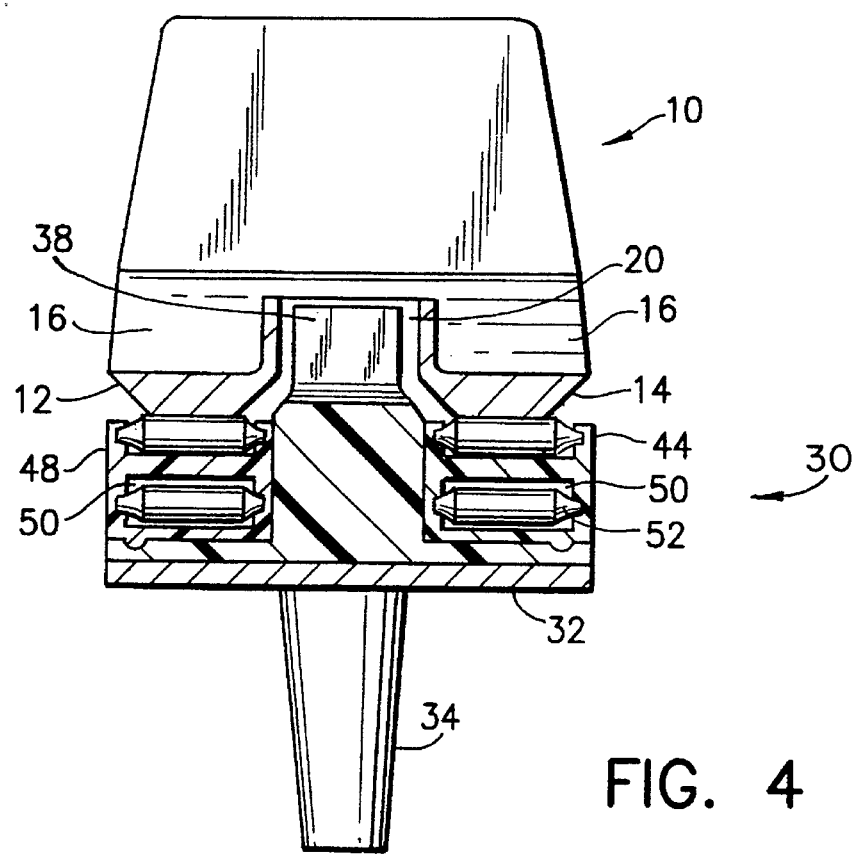
FIG. 4 is a cross-sectional view taken along line 4—4 in FIG. 2.
Figure 5:
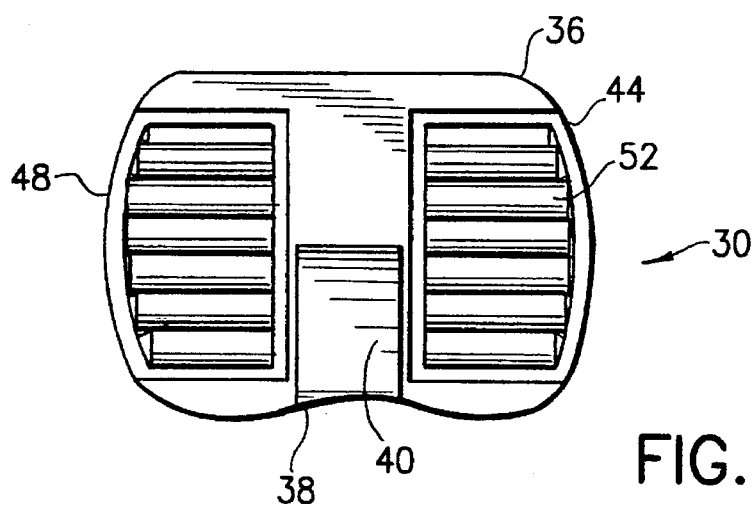
FIG. 5 is a top view of the tibial component of the artificial knee joint.

As will best be seen in FIGS. 4 and 5, the femoral component 10 has the condyle carriers 12 and 14 positioned for pivotal movement on the roller bearings 52 of the bearing units 44 and 48. The stabilizing post 38 allows rollback between the tibia and femur components, increasing flexion of the knee. The roller bearings move in the bearing races 50, so the rolling motion of the roller bearings in contact with the condylar bearing surfaces 22 and 24 considerably reduce friction therebetween, and therefore reduce wear.

Figure 7:
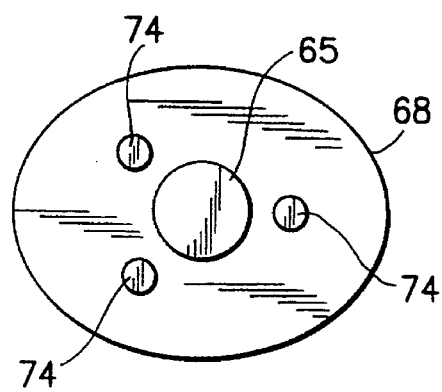
FIG. 7 is a bottom view of the patella component shown in FIG. 1.
Figure 8:
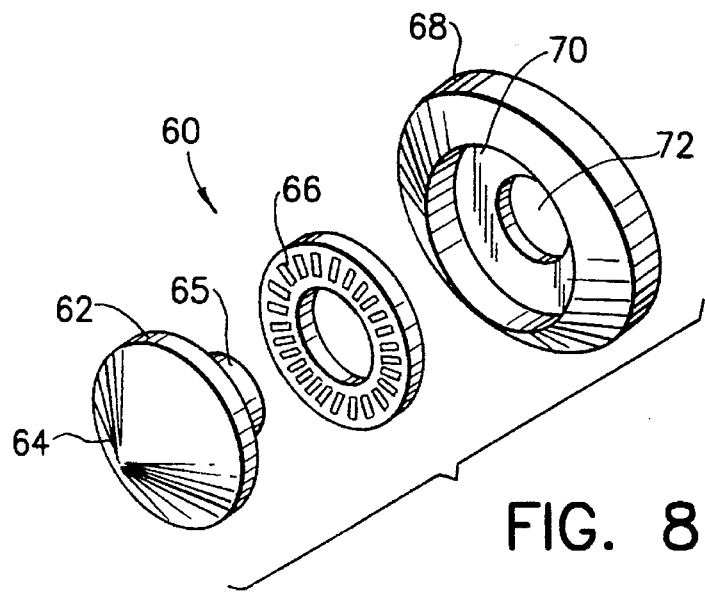
FIG. 8 is an exploded view of the patella component.
Figure 9:
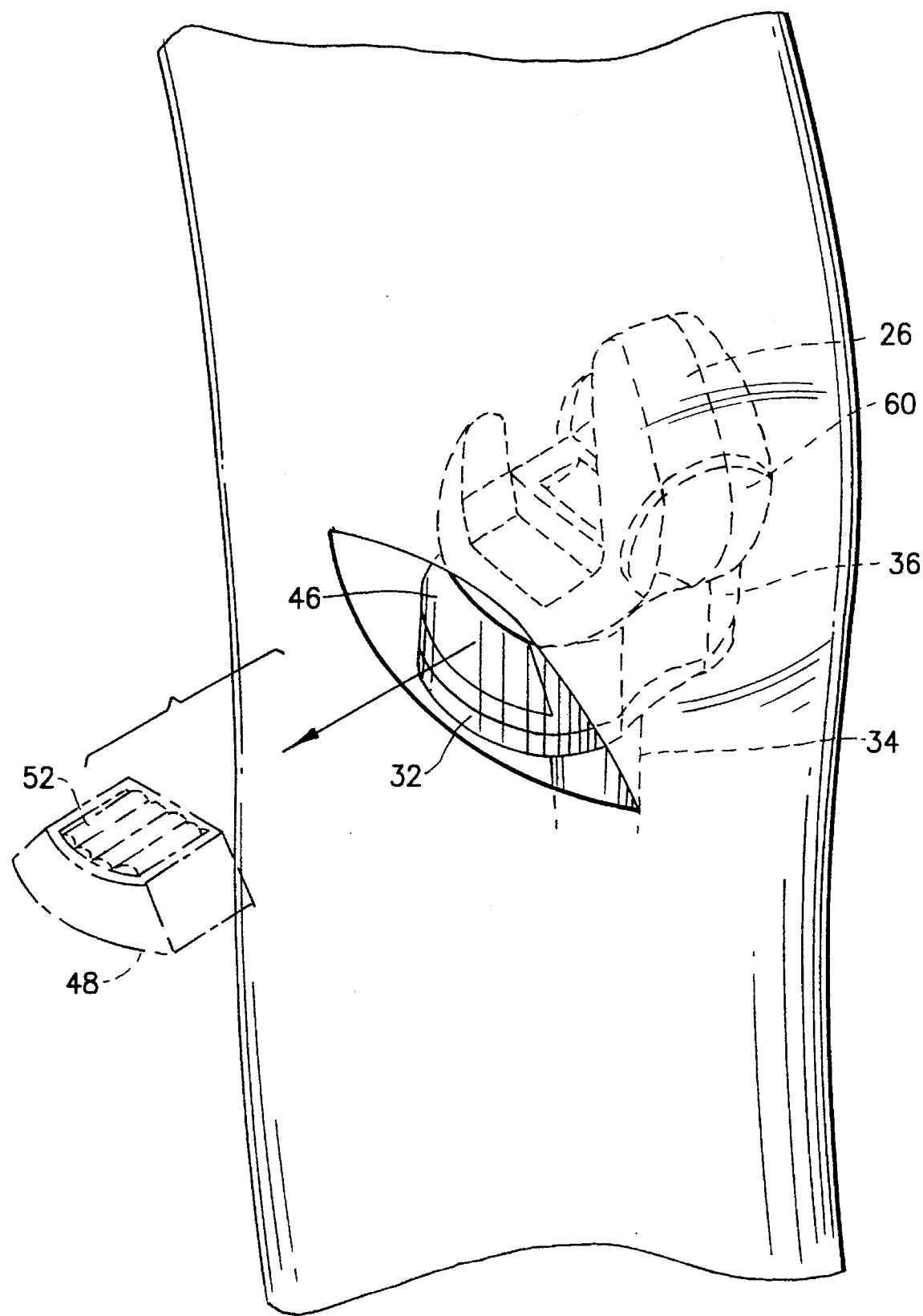
FIG. 9 illustrates the prosthetic knee joint partly in phantom positioned in the leg with an incision illustrating the replacement of one of the bearing units in the joint.

The patella component 60 which will best be seen in FIGS. 7 and 8 includes a patella button 62 having a conical shaped head 64 and a stem 65. A patella body member 68 has a socket 70 and a hole 72 therein. The patella button 62 is mounted in the socket 70 of the patella body member 68 on radial thrust roller bearings 66 with the stem 65 extending through the opening 72, as will best be seen in FIGS. 1 and 7. The body member 68 has a plurality of studs 74 extending therefrom which are adapted to receive and have mounted thereon the natural patella or a substitute therefor.

The natural patella moves over the femoral condyles at relatively constant distance from the tubercle of the tibia via the patella ligament attached to the patella. To simulate this action, the conical head 64 of the patella button 62 moves up and down in the anterior curved (concave groove) plate section 26 of the femoral component 10. The conical head 64 contacts the upstanding sidewalls of the concave groove of the plate section 26, thereby rotating the patella button to control and limit lateral excursion of the patella on flexion and extension of the knee.

Figure 6:
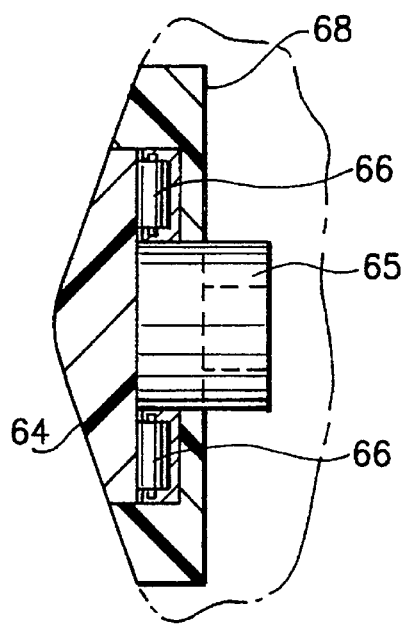
FIG. 6 is a cross-sectional view taken along line 6—6 of FIG. 1.

As is illustrated in FIG. 6, a feature of the present invention is the ability to remove a bearing unit 48 without requiring major reconstructive surgery. An incision can be made on either side of the prosthetic joint, and the bearing unit 48 as shown may be removed and replaced laterally from the bearing receptacle 46. The same could be accomplished from the right side of the artificial knee joint. Although the roller bearings cause less friction and would have a much longer life than the currently used roller bearing type liners, the ease of replacement is a considerable advantage over conventional prosthetic knee joints which require major reconstruction on breakdown.

Accordingly, a new and improved artificial knee joint is provided which eliminates a great deal of friction from the contact surface, thereby resulting in longer life with less chance of breakdown. In addition, the replacement of the roller bearings without requiring major reconstructive surgery is a breakthrough in prosthetic knee joint replacement.

Since other modifications and changes varied to fit particular operating requirements and environments will be apparent to those skilled in the art, the invention is not considered limited to the examples chosen for purposes of disclosure and covers all modifications and changes which do not constitute departures from the true spirit and scope of this invention.

What is claimed is:

1. A reduced friction knee joint prosthesis for simulating the natural movement between the femur and tibia of the user comprising:

a resurfacing femoral component having a pair of laterally spaced condyle carriers connected by an intercondylar connector, said condyle carriers being adapted to fit like a cap on resected femoral condyles on the femur of the user, a tibial component adapted to be mounted on a surgically prepared proximal tibia of the user having bearing mounting receptacle means therein, unitary bearing mounting means having bearing race means containing a plurality of movable and recirculating bearings in said bearing race means, said unitary bearing mounting means mounted in said bearing mounting receptacle means, whereby said unitary bearing mounting means can be readily replaced through a limited surgical incision through a coronal plane of the knee of the user, and said condyle carriers of said femoral component being positioned on said movable and recirculating bearings in said bearing mounting means in said bearing mounting receptacle means of said tibial component for pivotal movement of said condyle carriers on said plurality of movable and recirculating bearings in said tibial component.

2. The knee joint prosthesis as claimed in claim 1 wherein said bearing mounting receptacle means has lateral access entry and exit means for removably mounting said bearing mounting means containing said movable bearings on said tibial component.

3. The knee joint prosthesis as claimed in claim 1 wherein said bearing mounting receptable means has a pair of laterally disposed receptacles and a pair of bearing mounting means each having said bearing race means containing a plurality of roller bearings, said bearing mounting means being mounted in said pair of laterally disposed receptacles.

4. The knee joint prosthesis of claim 1 wherein said bearing mounting receptacle means contains retaining means for holding said bearing mounting in said tibial component.

5. The knee joint prosthesis as claimed in claim 3 wherein said bearing mounting receptacle means and said bearing mounting means have complimentary configurations for facilitating the insertion and removal of said bearing mounting means to and from said bearing mounting receptacle means.

6. The knee joint prosthesis as claimed in claim 1 wherein said unitary bearing mounting means comprises at least one unitary bearing mounting element containing said plurality of movable and recirculating bearings in said bearing race means.

7. The knee joint prosthesis as claimed in claim 1 wherein said unitary bearing mounting means comprises two unitary elements and said bearing mounting receptacle means comprises two laterally coronally spaced receptacles on said tibial component having a complimentary configuration with said two unitary elements for laterally removably receiving said two unitary elements.

8. A reduced friction knee joint prosthesis comprising:

a femoral component having a pair of laterally spaced condyle carriers connected by an intercondylar connector, said condyle carriers being adapted to house resected femoral condyles of the user, said condyle carriers being terminated in an anterior curved upwardly extending plate section having a concave recess therein adapted to receive the patella of the user, a tibial component adapted to be mounted on a surgically prepared proximal tibia of the user having a bearing mounting member, bearing mounting means having bearing race means containing a plurality of movable bearings mounted in said bearing mounting member, said condyle carriers of said femoral component being positioned on said movable bearings for pivotal movement of said femoral component on said movable bearings mounted in said tibial component, a patella component comprising a patella button, a radial thrust bearing means and a patella body for housing and positioning said patella button on said radial thrust bearing means, said patella body adapted to have the patella of the user mounted thereon, said patella button of patella component positioned in said concave recess on said femoral component for interaction therewith to simulate the movement of the natural patella.

* * * * *